United States Patent [19]

Shimizu et al.

[11] 4,355,111

[45] Oct. 19, 1982

[54] MICROORGANISM CULTURING DEVICE

[75] Inventors: Masaki Shimizu, Tokyo; Takeo Nomura, Hino, both of Japan

[73] Assignee: Terumo Corporation, Japan

[21] Appl. No.: 153,919

[22] Filed: May 28, 1980

[30] Foreign Application Priority Data

Jun. 4, 1979 [JP] Japan .................................. 54/69713
Apr. 1, 1980 [JP] Japan .................................. 55/42163

[51] Int. Cl.$^3$ ............................................. C12N 1/00
[52] U.S. Cl. ................................. 435/243; 215/248; 215/307; 215/310; 435/253; 435/296; 435/299; 435/801
[58] Field of Search .................... 435/4, 29, 30, 32, 33, 435/34, 243, 253, 296, 297, 298, 299, 300, 301, 801; 215/248, 307, 310

[56] References Cited

U.S. PATENT DOCUMENTS

| | | | |
|---|---|---|---|
| 2,161,097 | 6/1939 | Schröder-Nielsen | 215/307 |
| 3,297,184 | 1/1967 | Andelin | 215/307 |
| 3,901,402 | 8/1975 | Ayres | 215/248 |
| 4,070,249 | 1/1978 | Janin et al. | 435/300 X |
| 4,076,142 | 2/1978 | Naz | 215/307 |

FOREIGN PATENT DOCUMENTS

| | | | |
|---|---|---|---|
| 522210 | 10/1955 | Belgium | 215/307 |
| 91849 | 3/1938 | Norway | 215/307 |
| 1525969 | 9/1978 | United Kingdom | 215/307 |

*Primary Examiner*—Robert J. Warden
*Attorney, Agent, or Firm*—Bacon & Thomas

[57] ABSTRACT

A device for culturing microorganisms includes a vessel having a mouth for containing a culture medium and a stopper member for hermetically sealing the vessel. The stopper member is provided with a through hole on its peripheral wall for communicating with the inner atmosphere of said vessel.

19 Claims, 2 Drawing Figures

MICROORGANISM CULTURING DEVICE

BACKGROUND OF THE INVENTION

I. Field of the Invention

The present invention relates to a microorganism culturing device and, more particularly, to such a culturing device in which the inner atmosphere is maintained in a hermetically sealed state prior to culturing the microorganisms, and generated gases can be discharged, while maintaining the culturing conditions during the culturing process. It also relates to a method for culturing microorganisms using such a device.

II. Description of the Prior Art

Heretofore, the culture of anaerobic microorganisms has been carried out in culturing vessels completely sealed with elastic stoppers such as rubber stoppers, screw caps, seamers or the like.

In the culture of anaerobic microorganisms, however, when a collecting needle penetrates the stopper element for transplantation after incubation, the culture medium tends to spout through the needle due to the inner pressure. Further, the stoppers such as screw caps, seamers or the like tend to be blown off when they are being removed so that operators are often exposed to danger. Furthermore, when such incidents occur, outside air comes into contact with the culture medium so that bacteria in the air contaminate the medium.

Where stoppers with simple fastener members are used, the stoppers may often be blown off during incubation due to increased inner pressure in the culturing vessel produced by gases generated by the anaerobic microorganisms, whereby the culture medium becomes contaminated by bacteria in the open air.

Furthermore, the surrounding areas may become contaminated if the anaerobic organisms are scattered about when the stoppers blow off.

In the culture of aerobic microorganisms, on the other hand, the culturing vessels have been closed with stoppers which are permeable to air such as Morton caps, cotton plugs, aluminum caps, paper ball stoppers or the like. The culture of aerobic microorganisms, however, has several disadvantages: the culture medium cannot be stored for any length of time due to the air-permeability of the stopper of the culturing vessel; bacteria in the open air readily contaminate the medium by entering the open end of the vessel when the stopper is taken out for collection of the culture medium; there is difficulty in transporting culturing vessels with culture media due to leakage; and operators are exposed to danger as a result of this leakage.

In conventional culture methods, it is necessary to take out the stoppers when collecting samples. This, however, allows bacteria in the open air to invade the culturing vessel, so that the bacteria are incubated together with the culture organisms. This sometimes causes difficulty in distinguishing the culture organisms from the contaminating bacteria.

The culture of aerobic and anaerobic microorganisms in the same culturing vessels or devices has caused problems in that, when the airtight stoppers as mentioned hereinabove were used, the propagation of the aerobic microorganisms was hindered and, when the air-permeable stoppers were employed, the propagation of the anaerobic organisms was hindered. Accordingly, it has been necessary to utilize a separate culturing vessel or device for culturing aerobic and anaerobic microorganisms, respectively. This has increased the labor involved in culture procedures and made it difficult or impossible to carry out the culture in a rational, safe and sure way.

SUMMARY OF THE INVENTION

Accordingly, the primary object of the present invention is to provide a microorganism culturing device which permits the inner atmosphere to be maintained in a hermetically sealed state prior to the culture of the organisms, whereas during the culture, generated gases are discharged, while maintaining the culturing conditions.

Another object of the present invention is to provide a microorganism culturing device which allows the culture of either aerobic or anaerobic microorganisms.

A further object of the present invention is to provide a microorganism culturing device which has a simple construction and which may be operated easily.

A still further object of the present invention is to provide a method for culturing microorganisms using such a device.

The present invention provides a device for culturing microorganisms comprising a vessel with an opening, a medium contained in the vessel for culturing microorganisms, and a stopper member air-tightly sealing the vessel in the opening and having a through hole provided in the peripheral plane thereof for communication with the inner atmosphere of the vessel.

In one embodiment of the present invention, the stopper member is formed of a penetrable material, and the inside of the vessel is maintained at a reduced pressure.

In another embodiment of the present invention, the stopper member is provided in the peripheral plane thereof with an annular groove below the through hole.

The culture medium may be one which may be conveniently utilized for either aerobic or anaerobic microorganisms, but media which may suitably grow both aerobic and anaerobic microorganisms are preferable.

DETAILED DESCRIPTION OF THE PREFERRED EMBODIMENTS

The present invention will be described below in detail with reference to the attached drawings.

Figure 1:
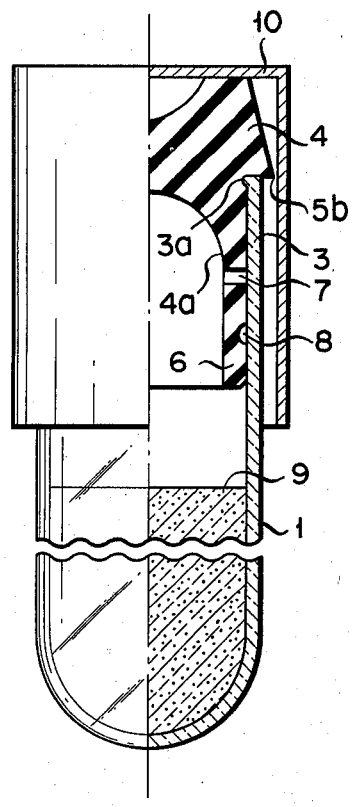
FIG. 1 is a partially sectional side view illustrating a microorganism culturing device in accordance with the present invention.

As illustrated in FIG. 1, a microorganism culturing device in accordance with the present invention includes a vessel or container 1 with a mouth or opening 3. The vessel 1 may be formed of any suitable material such as plastic, glass or the like; however, a transparent material, particularly glass is preferred in order to enable observation of the inside of the vessel during incubation. The shape of the vessel is not limited to a tube as illustrated in FIG. 1; it may be in any form, such as a bottle or flask form. As shown in the drawing, an annular projection 3a is provided on the inside periphery of the end portion of the vessel opening 3. This projecting portion may be formed by any suitable means such as burning the opening end portion.

A stopper member 4 forms an air-impermeable or air-tight seal at the opening portion 3 of the vessel 1.

Figure 2:
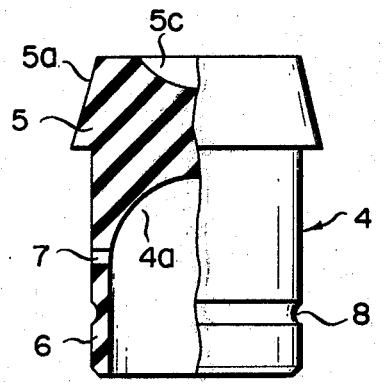
FIG. 2 is a partially sectional side view illustrating a stopper member used for the microorganism culturing device in accordance with the present invention.

The stopper member may be formed of any material which can supply air-impermeability, but a penetrable material, particularly a rubbery elastic material, is preferable. The stopper member 4 is constructed, as best shown in FIG. 2, with a recess 4a at the bottom portion; the recess 4a is so constructed as to form a relatively thin peripheral wall 6 constituting the stopper body portion. The peripheral wall 6 air-impermeably fits with the opening portion 3 of the vessel. The stopper body portion 6 is integrally formed with a head portion 5 having a slightly larger diameter than the body portion, and a peripheral wall 5a of the head portion is tapered away from the body portion 6. The head portion 5 is also provided with a recess 5c at its upper portion in order to further reduce the thickness of the head portion so that it will be more readily penetrable.

The body portion 6 is provided with a through hole 7 which communicates with the inner atmosphere in the vessel 1. The through hole 7, when viewed from the front, is in the form of a circle having a diameter of approximately 0.3 mm to 3 mm, or in an elliptical form having a minor axis of 0.3 mm to 2 mm and a major axis of 2 mm to 3 mm. There may be several through holes 7 formed in the body portion 6. Preferably, two circular holes, each having a diameter of 0.7 mm to 1.5 mm, are symmetrically disposed at a distance of 3 mm to 5 mm from the top of the body portion 6. An annular groove 8 is formed around the body portion 6 below the through hole 7.

The stopper member having the above-mentioned construction may be prepared by extruding preheated rubbery material under pressure into a mold and, upon solidifying, molding to provide a molded stopper having as yet no hole. Then a hole is made through the side wall portion with a hot needle having a predetermined shape and size or with a punch or the like. The stoppers thus prepared are then subjected to natural drying or drying at elevated temperatures. It is advantageous to subject the stopper elements to a coating treatment with silicone oil to facilitate insertion into the vessel.

Referring again to FIG. 1, the vessel 1 contains a medium 9 for culturing microorganisms. The medium 9 may be a culture medium suitable for culturing anaerobic microorganisms, such as brain-heart infusion medium as disclosed on page 895 of "Manual of Clinical Microbiology", 2nd Ed. edited by Edwin H. Lennette, Earle H. Spaulding and Joseph P. Truant, American Society for Microbiology, 1975, thioglycollate medium as described by Brewer in J. Amer. Ass. 115 598 (1940), brucella broth medium as described on page 896 of "Manual of Clinical Microbiology", 2nd Ed. or the like, or a medium suitable for culturing aerobic microorganisms, such as Columbia broth medium obtained by removal of agar from the medium described by Ellner et al. in Amer. J. Clin. Pathol 45 502 (1966), nutrient broth medium as recited on page 912 of "Manual of Clinical Microbiology", 2nd Ed., tryptic soy broth medium as disclosed on page 241 of "Shin Saikin Baichi Gaku Koza (New Handbook of Culture Media for Bacteria)", 1st Vol. by Sakazaki, K. K. Kindai Shuppan, Japan, 1978 or the like. For the object of the present invention, a medium which can grow both anaerobic and aerobic microorganisms is preferred. Such media are well known to those skilled in the art such as anaerobic basal culture medium formulated by Gifu Univ. described on page 338 of "Anaerobic Bacteria and Anaerobic Bacteria Disease" by Kosakai and Suzuki, Igaku shoin, Japan, 1968. The compositions of media suitable for use in the present invention are shown below as media A and B.

MEDIUM A

| Ingredients | Composition (g/liter of distilled water) |
| --- | --- |
| Tryptone | 5–20 |
| Soya peptone | 1–5 |
| Meat extract | 2–5 |
| Yeast extract | 3–10 |
| Liver digest | 0.5–2 |
| Glucose | 2–3 |
| Potassium phosphate, dibasic | 0.1–3 |
| Sodium chloride | 2–5 |
| L-cysteine hydrochloride | 0.35–0.5 |
| p-aminobenzoic acid | 0.04–0.06 |
| Sodium polyanethol sulfonate | 0.25–0.35 |
| Hemin | 0.003–0.007 |
| Agar | 0–0.01 |
| Gelatin | 10–14 |
| pH 7.3 ± 0.1 | |

MEDIUM B

To the medium A is added sodium bicarbonate in an amount of 1.5 to 2.5 grams per liter of distilled water.

In the media A and B, polypeptone may be substituted for tryptone, animal meat peptone for meat extract, sodium phosphate, dibasic for potassium phosphate, dibasic, and dextran for gelatin.

The following compositions C and D provide particularly suitable media.

MEDIUM C

| Ingredients | Composition |
| --- | --- |
| Typtone | 17 g |
| Soya peptone | 3 g |
| Meat extract | 3 g |
| Yeast extract | 5 g |
| Liver digest | 1 g |
| Glucose | 2.5 g |
| Potassium phosphate, dibasic | 2.5 g |
| Sodium chloride | 5 g |
| L—cysteine hydrochloride | 0.45 g |
| p-aminobenzoic acid | 0.05 g |
| Sodium polyanethol sulfonate | 0.35 g |
| Hemin | 0.005 g |
| Agar | 0.01 g |
| Gelatin | 12 g |
| Distilled water | 1,000 ml |
| pH 7.3 ± 0.1 | |

MEDIUM D

| Ingredients | Composition |
| --- | --- |
| Typtone | 10 g |
| Soya peptone | 3 g |
| Meat extract | 3 g |
| Liver digest | 1 g |
| Yeast extract | 5 g |
| Glucose | 2.5 g |
| Potassium phosphate, dibasic | 0.15 g |
| Sodium chloride | 4.0 g |
| L—cysteine hydrochloride | 0.45 g |
| p-aminobenzoic acid | 0.05 g |
| Sodium polyanethol sulfonate | 0.25 g |
| Sodium bicarbonate | 2 g |
| Hemin | 0.005 g |
| Gelatin | 12 g |
| Distilled water | 1,000 ml |

-continued

| Ingredients | Composition |
|---|---|
| pH 7.3 ± 0.2 | |

The media A, B, C and D may be prepared by the following procedures. The ingredients other than gelatin are weighed and dissolved in 500 ml of distilled water. The predetermined amounts of L-cysteine hydrochloride and hemin are dissolved in 0.01 N hydrochloric acid and water, respectively, before being added to the solution. Another solution is prepared by weighing the gelatin and dissolving it in 500 ml of distilled water while warming. Both solutions are mixed well and cooled to room temperature. The solution is then adjusted with an alkaline solution such as 2 N aqueous sodium hydroxide solution to the predetermined pH value and pre-filtered on absorbent cotton. The resulting filtrate is then filtered on a glass filter under reduced pressure, and the filtrate is utilized as a medium.

The inside of the vessel 1 is maintained at a predetermined reduced pressure, i.e. at a pressure so as to enable a predetermined amount of liquid sample containing microorganisms to be sucked in. A covering 10 for enclosing the outside of the stopper member 4 and the vessel opening 3 is provided, leaving a small gap between it and the lower projection 5b of the head portion 5 of the stopper member 4.

The covering 10 does not inhibit movement of the stopper member 4 and may be formed of any material such as plastic, aluminum or the like.

The device for culturing microorganisms in accordance with the present invention having the above construction may be prepared as follows:

A 20 ml tube (diameter, 15.5 mm; length, 165 mm) or a suitable vessel in the form of a flask or a bottle is filled with a predetermined amount of a medium (18 ml for a 20 ml tube, or 45 ml for a 50 ml flask-like or bottle-like vessel). After the vessel is evacuated by reducing the pressure, a mixed gas (nitrogen:carbon dioxide=9:1) is introduced to give a nearly normal pressure, and the pressure is then reduced to permit a predetermined amount of the medium to be sucked in. Thereafter, a stopper member is inserted into the opening of the vessel for sealing under reduced pressure. The vessel is then sterilized in a high temperature, high pressure steam sterilizer at a temperature of 115° to 121° C. and a pressure of 1.5 to 2 kg/cm$^2$ for a period of 15 to 20 minutes.

The culture of microorganisms using this device may be carried out by first collecting a liquid sample containing the microorganism, for example, a patient's blood, and introducing the sample in the vessel. It is preferable to use a holder for vacuum blood collecting tube for this purpose (manufactured by TERUMO Corporation). The holder is composed of a hollow body capable of accommodating the microorganism culturing device and a needle for collecting a sample which is supported by the end portion of the hollow body and constructed so as to form a needle tip at both ends. After the stopper member of the device has been disinfected by alcohol, tincture of iodine, or the like, the culturing device is inserted into the holder having the sample collecting needle. One tip of the sample collecting needle is injected into the vein of a patient, and the other tip is inserted into the vessel through the stopper member by, inserting the device deeply into the holder, so that a predetermined amount of blood is sucked into the culturing device by the reduced pressure of the device. In another embodiment, a syringe may be used to practice the invention. In this case, the syringe is used to collect a sample and is then inserted into the center of the disinfected stopper member of the culturing device. As the culturing device is maintained under reduced pressure, a predetermined amount of the sample is automatically drawn from the syringe into the device through suction.

After the sample is collected and drawn into the device, incubation of the anaerobic culture may be carried out at 27° to 37° C. for 1 to 14 days. If necessary, incubation may be further continued. Produced gases may be easily discharged by rotating the stopper member one revolution to improve slidability of the stopper member.

In an anaerobic culture, the anaerobic microorganisms may produce gases during incubation, increasing the pressure inside the vessel 1. When the pressure is increased above a certain level, it will force the stopper member up to a point where the through hole 7 reaches or slightly surpasses the top of the opening 3 of the vessel 1. As the stopper member reaches this point, the gases are discharged through the through hole 7 to the outside of the vessel, and the upward movement of the stopper member stops there. Even if the stopper member 4 happened to be further forced up by the gases generated in the vessel, the annular projection 3a of the vessel opening would fit into the annular groove 8 provided around the body portion 6 of the stopper member to stop further upward movement of the stopper member 4. After the gases are discharged, the stopper member 4 may be forced down manually to close the through hole 7 with the inner wall of the opening portion of the culturing vessel 1 so that the vessel 1 may again maintain an airtight closure. Accordingly, the culturing device according to the present invention permits the generated gases to be discharged while a substantially airtight condition is maintained. It further prevents the stopper member 4 from being blown off during or after incubation by the gases generated in the vessel, and the medium is contained in the vessel without leaking so that it can be handled with safety.

In an aerobic culture, on the other hand, the culture may be carried out under the same culturing conditions as in anaerobic culture by collecting a sample as mentioned above, pulling the stopper member 4 up to a level at which the through hole 7 comes out partly or wholly over the top portion of the opening 3 of the culturing vessel 1 and attaching the covering 10. Accordingly, the culturing device according to the present invention permits communication of the inside of the vessel with an outside atmosphere such as air outside the vessel while in a condition where the stopper member 4 is attached to the opening 3 of the culturing vessel 1, yet prevents the medium in the vessel from being contaminated.

The following examples illustrate the culture of a variety of microorganisms using the culturing device according to the present invention as shown in FIG. 1.

EXAMPLE 1

A suspension of a gas producing strain, as illustrated in Tables 1 and 2, in an appropriate amount of distilled water was prepared so as to contain from 10 to $10^2$ CFU/ml and 2 ml of the spore suspension was collected in the vessel 1 and incubated at 37° C. The device was observed daily for growth of the microorganisms of the cultured strain in the culturing vessel and for movement of the stopper member due to gas pressure. The results are shown in Tables 1 and 2. The movement of the stopper member is indicated herein as the number of days required for part or all of the hole portion of the stopper member to move to the opening top of the culturing device. No further movement of the stopper member after the days required for the above-stated movement was noted upon further incubation.

TABLE 1

(Culture in Medium C)

| Culture Strains | Growth of Strain | Movement of Stopper |
|---|---|---|
| Escherichia coli NIHJ | Excellent | 2 Days |
| Citrobacter freundii ATCC 8090 | " | 1 Day |
| Salmonella typhimurium IID 971 | " | 2 Days |
| Salmonella paratyphi IID 605 | " | 1 Day |
| Salmonella enteritidis IID 604 | " | 2 Day |
| Arizona arizonae ATCC 13314 | " | 2 Days |
| Salmonella pullorum 3H-2 | " | 2 Days |
| Klebsiella pneumoniae IID 875 | " | 2 Days |
| Enterobacter cloacae IAM 1624 | " | 2 Days |
| Enterobacter aerogenes RIMD 0502001 | " | 1 Day |
| Hafnia alvei ATCC 13337 | " | 3 Days |
| Proteus morganii IID 602 | " | 2 Days |
| Proteus mirabilis RIMD 1641002 | " | 2 Days |
| Bacillus macerans IFO 3490 | " | 4 Days |
| Clostridium tetani IID 524 | " | 8 Days |
| Clostridium sporogenes IAM 19235 | " | 2 Days |
| Clostridium sphenoides | " | 1 Day |

TABLE 2

(Culture in Medium D)

| Culture Strains | Growth of Strain | Movement of Stopper |
|---|---|---|
| Escherichia coli NIHJ | Excellent | 2 Days |
| Citrobacter freundii ATCC 8090 | " | 1 Day |
| Salmonella typhimurium IID 971 | " | 2 Days |
| Salmonella paratyphi IID 605 | " | 1 Day |
| Salmonella enteritidis IID 604 | " | 2 Days |
| Arizona arizonae ATCC 13314 | " | 2 Days |
| Salmonella pullorum 3H-2 | " | 2 Days |
| Klebsiella pneumonia IID 875 | " | 2 Days |
| Enterobacter cloacae IAM 1624 | " | 2 Days |
| Enterobacter aerogenes RIMD 0502001 | " | 1 Day |
| Hafnia alvei ATCC 13337 | " | 3 Days |
| Proteus morganii IID 602 | " | 2 Days |
| Proteus mirabilis RIMD 1641002 | " | 2 Days |
| Bacillus macerans IFO 3490 | " | 4 Days |
| Clostridium tetani IID 524 | " | 8 Days |
| Clostridium sporogenes IAM 19235 | " | 2 Days |
| Clostridium sphenoides | " | 1 Day |
| Veillonella alcallecens ATCC 17745 | Favorable | 4 Days |
| Fusobacterium necrophorum RIMD 0623001 | Excellent | 1 Day |
| Fusobacterium varium ATCC 8501 | " | 1 Day |
| Bacteroides melaninogenicus | | |

TABLE 2-continued (Culture in Medium D)

| Culture Strains | Growth of Strain | Movement of Stopper |
|---|---|---|
| RIMD 0230004 | " | 1 Day |

EXAMPLE 2

A suspension for each strain illustrated in Tables 3 and 4 was prepared in an appropriate amount of distilled water so as to contain approximately $1 \times 10^1$ to $5 \times 10^1$ CFU/ml. The suspensions were collected and inserted into the respective media. An incubation was carried out at 37° C. after pulling the stopper member up so as to bring the hole of the stopper member over the opening of the vessel. The culture media were measured after two days of incubation for the number of viable microorganisms, in a conventional manner. The results are shown in Tables 3 and 4, indicating a good growth of $10^7$ to $10^9$ CFU/ml.

As a control, culture systems having the same construction were maintained at 37° C. for 21 days without any culture strain added. The vessels were in an aeration condition as stated hereinabove, with or without the cover. In this case, no contamination of bacteria in the open air was found.

TABLE 3

(Culture in Medium C)

| Culture Strains | Numbers of Microorganisms Inoculated CFU/ml | Numbers of Viable Microorganisms CFU/ml |
|---|---|---|
| Pseudomonas aeruginosa | $1.5 \times 10$ | $1 \times 10^8$ |
| Escherichia coli NIHJ | $1.0 \times 10$ | $7 \times 10^8$ |
| Salmonella enteritidis IID 604 | $1.3 \times 10$ | $2 \times 10^9$ |
| Shigella sonnei IID 969 | $1.0 \times 10$ | $4 \times 10^8$ |
| Enterobacter cloacae IAM 1624 | $1.7 \times 10$ | $2 \times 10^9$ |
| Proteus mirabilis RIMD 1641002 | $9.0 \times 10$ | $1 \ 10^9$ |
| Staphylococcus aureus ATCC 6538P | $0.5 \times 10$ | $2 \times 10^7$ |
| Streptococcus pyogenes IID 693 | $0.2 \times 10$ | $1 \times 10^9$ |
| Blank (with cover) | — | No growth |
| Blank (without cover) | — | No growth |

TABLE 4

(Culture in Medium D)

| Culture Strains | Numbers of Microorganisms Inoculated CFU/ml | Numbers of Viable Microorganisms CFU/ml |
|---|---|---|
| Pseudomonas aeruginosa IID 1001 | $4.5 \times 10$ | $4 \times 10^8$ |
| Pseudomonas maltophila IID 1275 | $4.7 \times 10$ | $4 \times 10^8$ |
| Achromobacter xylosoxidans ATCC 27061 | $1.6 \times 10$ | $1 \times 10^9$ |
| Escherichia coli NIHJ | $0.5 \times 10$ | $3 \times 10^9$ |
| Shigella sonnei IID 969 | $1.3 \times 10$ | $1 \times 10^9$ |
| Enterobacter cloacae IAM 1624 | $2.3 \times 10$ | $3 \times 10^9$ |
| Proteus mirabilis RIMD 1641002 | $1.9 \times 10$ | $3 \times 10^9$ |
| Staphylococcus aureus ATCC 6538P | $5.3 \times 10$ | $5 \times 10^8$ |
| Streptococcus pyogenes IID 693 | $1.2 \times 10$ | $5 \times 10^9$ |
| Bacillus subtilis ATCC 6633 | $7.1 \times 10$ | $3 \times 10^8$ |

TABLE 4-continued (Culture in Medium D)

| Culture Strains | Numbers of Microorganisms Inoculated CFU/ml | Numbers of Viable Microorganisms CFU/ml |
|---|---|---|
| Listeria monocytogenes IID 579 | $3.4 \times 10$ | $5 \times 10^8$ |
| Salmonella enteritidis IID 604 | $1.9 \times 10$ | $1 \times 10^9$ |
| Clostridium tetani IID 524 | $1.2 \times 10$ | $7 \times 10^8$ |
| Fusobacterium necrophorum RIMD 0623001 | $3.4 \times 10$ | $8 \times 10^8$ |
| Bacterodies fragilis ss. fragilis RIMD 0230001 | $2.1 \times 10$ | $6 \times 10^7$ |
| Neisseria meningitidis ATCC 13090* | $6.0 \times 10$ | $5 \times 10^7$ |
| Blank (with cover) | — | No growth |
| Blank (without cover) | — | No growth |

*A suspension of microorganism was prepared by substituting human blood for distilled water.

EXAMPLE 3

A suspension for each strain illustrated in Tables 5 and 6 was prepared in an appropriate amount of distilled water so as to contain approximately $1 \times 10^1$ to $5 \times 10^2$ CFU/ml and then were used for tests.

In the case aerobic cultures, incubation was started after the hole of the stopper was pulled up over the opening of the culturing vessel and, in the case of the anaerobic cultures, incubation was carried out at a temperature of 37° C. without pulling up the stopper. The culture media, respectively, were measured for the number of spores in a conventional manner, and this was recorded as the number of days required for reaching approximately $5 \times 10^7$ CFU/ml or more. The results are shown in Table 5 (anaerobic culture) and Table 6 (aerobic culture), indicating that some of the culture strains grew better on Medium D than on Medium C.

TABLE 5

| | Anaerobic Culture | | |
|---|---|---|---|
| | | Days Required for Growing to $5 \times 10^7$ CFU/ml Viable Microorganisms or More | |
| Culture Strains | Number of Microorganisms Inoculated CFU/ml | Medium C | Medium D |
| Pseudomonas aeruginosa IID 1001 | $4.5 \times 10^2$ | 2 | 1 |
| Pseudomonas fluorescens IFO 12055 | $3.4 \times 10^1$ | 2 | 1 |
| Neisseria meningitidis ATCC 13090 | $6.0 \times 10^*$ | 4 | 2 |
| Neisseria gonorrhoeae IID 828 | $1.0 \times 10^*$ | 5 | 3 |

*The suspension of microorganisms was prepared by using human blood in place of distilled water.

TABLE 6

| | Aerobic Culture | | |
|---|---|---|---|
| | | Days Required for Growing to $5 \times 10^7$ CFU/ml Viable Microorganisms or More | |
| Culture Strains | Number of Microorganisms Inoculated CFU/ml | Medium C | Medium D |
| Staphylococcus epidermidis ATCC 12228 | $3.8 \times 10^1$ | No Growth* | 2 |
| Fusobacterium nucleatum IID 891 | $2.0 \times 10^1$ | No Growth* | 2 |
| Fusobacterium varium ATCC 8501 | $1.2 \times 10^1$ | No Growth | 1 |
| Bacteroides fragilis ss. distasonis RIMD 0230002 | $3.4 \times 10^1$ | No Growth* | 1 |
| Peptostreptococcus micros RIMD 1636001 | $2.5 \times 10^2$ | No Growth* | 3 |
| Peptostreptococcus parvulus RIMD 1637001 | $2.6 \times 10^1$ | No Growth * | 3 |
| Bifidobacterium adolescentis ATCC 15705 | $1.5 \times 10^2$ | 3 | 1 |

*Observation for 7 days

In accordance with the present invention, gases generated during incubation of an anaerobic culture can be easily discharged through the hole in the stopper member. With the same system, an aerobic culture can also be incubated merely by pulling up the stopper member so as to position a part or whole of the through hole over the tip end of the opening portion of the culturing vessel. Thus, the system having the same stopper and culture medium can be utilized for both anaerobic and aerobic cultures. With this stopper member, incubation can be carried out with safety and certainty because the stopper member tends not to be blown off and the medium is not scattered about. Furthermore, the system according to the present invention does not require the employment of other accessories for discharge of gases or aeration so that manufacture of the device is easy and inexpensive. The device in accordance with the present invention can achieve various advantages as mentioned above.

What we claim is:

1. A microorganism culturing device comprising:
a vessel with an opening, said vessel having a projection at the inner portion of said opening;
a culture medium contained in said vessel for culturing microorganisms; and,
a stopper member hermetically sealing said vessel in the opening thereof, said stopper member having a through hole for communicating with the inner atmosphere of said vessel, said through hole having one end open at a side wall of said stopper, said stopper member further having an annular groove around the peripheral well below the through hole engageable with the projection at the inner portion of the opening on the vessel;
wherein said stopper member is readily slidable along the inner wall of said vessel by means of gas pressure exerted on said stopper from within said vessel, to a point where said through hole establishes communication of the inside atmosphere of said vessel with the outside atmosphere at or above the tip end of said vessel;
whereby said through hole is in a state of being closed by the inner wall of said vessel at the start of the culturing, preventing communication of the inside atmosphere of said vessel with the outside atmosphere, and establishes communication of the inside atmosphere of said vessel with the outside atmosphere by forcing said stopper member upwards by means of the pressure on the gases produced during culturing to shift said one end of the through hole to or above a tip end of said vessel, thereby discharging said gases from the inside of said vessel to the outside through said through hole.

2. A device as claimed in claim 1, wherein the stopper member has a recess in the bottom portion thereof to thereby provide a relatively thin peripheral wall and has the through hole in said peripheral wall.

3. A device as claimed in claim 2, wherein the stopper member has a recess at the upper end portion thereof.

4. A device as claimed in claims 2 or 3, wherein the inside of the vessel is maintained under reduced pressure.

5. A device as claimed in claim 4, wherein the stopper member is made of a penetrable material.

6. A device as claimed in claim 5, wherein the stopper member is made of a rubbery elastic material.

7. A device as claimed in claim 1, wherein the culture medium is a medium for culturing anaerobic microorganisms.

8. A device as claimed in claim 7, wherein the culture medium is brain-heart infusion medium, thioglycollate medium or brucella broth medium.

9. A device as claimed in claim 1, wherein the culture medium is a medium for culturing aerobic microorganisms.

10. A device as claimed in claim 9, wherein the culture medium comprises tryptone, soya peptone, meat extract, yeast extract, liver digest, glucose, potassium phosphate, dibasic, L-cysteine hydrochloride, p-aminobenzoic acid, sodium polyanethol sulfonate, hemin, agar and gelatin.

11. A device as claimed in claim 9, wherein the medium is composed of tryptone, soya peptone, meat extract, yeast extract, liver digest, glucose, potassium phosphate, dibasic, L-cystein hydrochloride, p-aminobenzoic acid, sodium polyanethol sulfonate, hemin, gelatin and either agar or sodium bicarbonate.

12. A device as claimed in claim 1, wherein the culture medium is a medium capable of culturing both of anaerobic and aerobic microorganisms.

13. A method for culturing a microorganism comprising: introducing a sample containing at least anaerobic microorganism into a microorganism culturing device comprising a vessel having an opening and containing a culture medium, and a stopper member having at a fitting side wall thereof a through hole capable of communication with the inside of the vessel and sealing the vessel in the opening thereof, and culturing the anaerobic microorganism; wherein the stopper member is forced upwards by the pressure exerted by the gases produced in the vessel during culturing to shift the through hole to or above a tip end of the vessel thereby discharging the gases through the through hole to the outside of the vessel and wherein the inside of the vessel is initially maintained under reduced pressure such that the sample is introduced into said vessel by being sucked into said vessel.

14. A method for culturing an anaerobic microorganism comprising: providing a microorganism culturing device comprising a vessel with an opening, a culture medium contained in said vessel for culturing microorganisms, and a stopper member hermetically sealing said vessel in the opening thereof and having a through hole having one end open at a side wall of said stopper member for communicating with the inner atmosphere of said vessel and maintaining the inside of said vessel under reduced pressure; introducing a liquid sample containing an anaerobic microorganism into the vessel said liquid sample being sucked into said vessel by virtue of the reduced pressure inside said vessel; and culturing the anaerobic microorganism with the through hole closed by the inner wall of the vessel, wherein, during culturing, when gases produced by propagation of the anaerobic microorganism exceeds a certain pressure level, the stopper member is forced upward such that a part or whole of the through hole reaches a position above the tip end of the vessel, whereby the inside and the outside of the vessel communicate with each other and the gases are discharged to the outside of the vessel through the through hole.

15. A method for culturing a microorganism comprising: providing a microorganism culturing device comprising a vessel with an opening, said vessel having a projection at the inner portion of said opening, a culture medium contained in said vessel for culturing microorganisms, and a stopper member hermetically sealing said vessel in the opening thereof, said stopper member having a through hole having one end open at a side wall of said stopper member for communicating with the inner atmosphere of said vessel, said stopper member further having an annular groove around the peripheral wall below the through hole engageable with the projection at the inner portion of the opening on the vessel; introducing a liquid sample containing at least aerobic microorganism into the vessel; and culturing the aerobic microorganism with the inside atmosphere of the vessel communicated with the outside atmosphere of the vessel by a part or whole of the through hole occupying a position above the tip end of the vessel.

16. A method as claimed in claims 13, 14 or 15, wherein the device is sterilized by means of high temperature, high pressure steam prior to introducing said sample.

17. A method as claimed in claims 13, 14 or 15, wherein the inside atmosphere of said vessel is constituted by a mixed gas of carbon dioxide and nitrogen.

18. A method as claimed in claims 13, 14 or 15, wherein said sample is a blood.

19. A method as claimed in claims 13, 14 or 15, wherein said culturing is carried out at a temperature from 27° C. to 37° C. for one to fourteen days.

* * * * *